United States Patent
Weinstein

[11] Patent Number: 5,961,500
[45] Date of Patent: Oct. 5, 1999

[54] PREWETTED MEDICAL WIPE WITH IMPERMEABLE BARRIER

[76] Inventor: Robert E. Weinstein, 177 Commonwealth Ave., Boston, Mass. 02116

[21] Appl. No.: 09/008,416

[22] Filed: Jan. 16, 1998

Related U.S. Application Data

[63] Continuation-in-part of application No. 08/789,628, Jan. 27, 1997, abandoned.

[51] Int. Cl.⁶ .......................... A61M 35/00; A61F 13/00
[52] U.S. Cl. .......................... 604/304; 604/306; 604/289; 602/48
[58] Field of Search ..................................... 604/289, 290, 604/293, 303, 306, 304, 308, 312, 360, 385.1; 602/48, 56–58; 128/155, 156, 888; 401/132; 15/104.93

[56] References Cited

U.S. PATENT DOCUMENTS

| | | |
|---|---|---|
| 2,840,080 | 6/1958 | Clark . |
| 2,999,265 | 9/1961 | Duane et al. . |
| 3,363,625 | 1/1968 | Jovis . |
| 4,427,111 | 1/1984 | Laipply . |
| 4,588,400 | 5/1986 | Ring et al. . |
| 4,631,227 | 12/1986 | Nakamura . |
| 4,696,393 | 9/1987 | Laipply . |
| 4,829,995 | 5/1989 | Metters . |
| 4,925,453 | 5/1990 | Kannakeril . |
| 5,009,652 | 4/1991 | Morgan et al. . |
| 5,115,801 | 5/1992 | Cartmell et al. . |
| 5,562,642 | 10/1996 | Smith et al. . |

*Primary Examiner*—Ronald Stright
*Assistant Examiner*—David J. Cho
*Attorney, Agent, or Firm*—Morse & Altman

[57] ABSTRACT

A wetted, disposable wipe constructed by bonding a layer of absorbent material to one side of a barrier sheet that is impermeable to infectious agents and insoluble in dermatological fluids, filling a reservoir in the barrier with a dermatological fluid, and hermetically sealing the absorbent layer between the barrier and a cover. The peripheral edges of the absorbent layer are spaced inwardly from the peripheral edges of the barrier to provide a surrounding zone of the impermeable barrier alone. The absorbent layer bond to the barrier is resistant to degradation caused by exposure to the dermatological fluid. The cover is secured by an adhesive that is resistant to degradation caused by exposure to the dermatological fluid and that allows the cover to be manually peeled from the barrier. The reservoir holds the dermatological fluid temporarily to prevent vapors from the fluid from igniting during the barrier/cover sealing process.

12 Claims, 2 Drawing Sheets

PREWETTED MEDICAL WIPE WITH IMPERMEABLE BARRIER

RELATED APPLICATIONS

The present application is a continuation-in-part application of Application No. Ser. 08/789,628, dated Jan. 27, 1997 for PREWETTED MEDICAL WIPE WITH IMPERMEABLE BARRIER in the name of Robert E. Weinstein now abandoned.

BACKGROUND OF THE INVENTION

1. Field of the Invention

The present invention relates to wipes, more specifically, to prewetted, disposable absorbent wipes that have a barrier that is impermeable to infectious agents.

2. The Prior Art

Applying fluidic dermatological materials, such as antiseptics, creams, ointments, and cosmetics, to intact, disrupted, or diseased skin and wiping unwanted materials from the skin are normal medical and personal hygiene procedures. This is usually done by means of an applicator, swab, or wipe (collectively, a wipe). Typically, the wipe contains only an amount of porous absorbent material, for example, a square or ball of cotton. Until relatively recently, there was no satisfactory solution to the problem of body fluids migrating from one side of the wipe to the other. The migration would occur either through the wipe or laterally on one side of the wipe and seeping over the peripheral edges to reach the opposite side of the wipe. If the person holding the wipe was not using some form of protection, such as rubber gloves, or the protection was defective, this migration exposed both the person doing the wiping and the person being wiped to the body fluids of the other, which may be contaminated by infectious agents. Even a person applying dermatologicals to himself or herself may be putting themselves at risk. For example, if the person uses a wipe on his diseased skin and then rubs his eye, he may transfer an infectious agent to the eye.

A solution to the body fluid migration is suggested by the disclosure of U.S. Pat. No. 5,009,652, issued to Morgan et al. Morgan discloses a wipe with an absorbent layer laminated to a layer that is impermeable to infectious agents. The impermeable layer is larger in area than the absorbent layer such that the impermeable layer extends beyond the periphery of the absorbent layer.

Early wipes were dipped into a container of the desired fluid, immediately applied to the body, and disposed of after one use. More recently, in order to render the procedure more convenient and sterile, prewetted disposable wipes have been available. Prewetted wipes are moistened with the desired fluid during the manufacturing process and sealed into a foil or foil/plastic laminate pouch. The pouch is opened to reveal the moistened wipe, used, and disposed of.

The wipe of Morgan may be used as described above, where the wipe is moistened, used immediately, and disposed of. However, the convenience and sterility of the packaged, prewetted wipe is lost.

SUMMARY OF THE INVENTION

An object of the present invention is to provide a prewetted and sterile wipe that has a barrier impermeable to infectious agents.

The wetted, disposable wipe of the present invention is constructed by bonding a layer of absorbent material to one side of an impermeable barrier, wetting the absorbent layer with a desired dermatological fluid, and sealing the absorbent layer so that the dermatological fluid does not evaporate and so that the absorbent layer maintains its sterility.

The barrier is a sheet composed of a synthetic resin film that is impermeable to infectious agents, is not wettable by water, and is insoluble in water, body fluids, and solutions of common antiseptics, such as isopropyl alcohol. These resin films include polyolefins and polyvinyl copolymers. Preferred materials include those that are resistant to degradation caused by exposure to either wateror alcohol-based fluids.

If the absorbent layer is secured to the barrier such that when the peripheral edges of both are contiguous, the body fluids absorbed by the absorbent layer can wick around the edges and reach the side of the wipe that is being held. To prevent this migration, the peripheral edges of the absorbent layer are spaced inwardly from the peripheral edges of the barrier to provide a surrounding zone of the impermeable barrier alone.

Optionally, the barrier is reinforced on its periphery with a peripheral ridge around the edges on one or both surfaces of the barrier. The ridge helps to prevent the collapse of the nonwettable periphery of the barrier, and the moat created by this ridge provides an additional trap for body fluids.

The absorbent layer is composed of a porous material, such as gauze cotton, prepared cotton, other organic fibers such as wood fibers, rayon, open-meshed cloth of varying degrees of fineness, woven and non-woven synthetic fibers, and foamed polymers such as polyurethane, that maintains its integrity when moistened. The absorbent layer is bonded to the barrier by techniques well known in the art of adhesives, such as heat lamination and applying a thin coat of molten polyolefin to the barrier and pressing the absorbent layer to it before the coat solidifies. The bond is resistant to degradation caused by exposure to the utilized dermatological fluid.

The wetted absorbent layer is hermetically sealed into an enclosed space between the barrier and a removable cover. The cover is a planar sheet that is preferably composed of a metal foil, a plastic, or a laminate of both. The cover is unaffected by water and the dermatological fluid during the shelf life of the wipe. The cover is secured to the barrier by an adhesive that is strong enough to maintain the hermetic seal, but weak enough so that the cover can be manually peeled from the barrier. The adhesive is unaffected by water and the dermatological fluid during the shelf life of the wipe. The preferred adhesives include a low-melting-point, toluene-treated polyolefin. Optionally, a tab extends from one edge of the cover for ease in peeling the cover off.

The absorbent layer is prewetted by filling a reservoir in the barrier sheet approximately in the center of the absorbent layer with the dermatological fluid prior to or after bonding the absorbent layer to the barrier. The fluid is absorbed into the absorbent layer before the wipe is needed for use.

The wipe is held in one of several contemplated ways. In the first, the flexibility of the wipe allows a person to merely grasp the barrier, causing the wipe to crumple between the fingers, providing a handle. In the second, a flap extending from the barrier handle surface provides a handle. In the third, another layer of absorbent material is bonded to the barrier handle surface to provide a nonslip surface for grasping. In the fourth, the fluid reservoir can double as a handle.

Other objects of the present invention will become apparent in light of the following drawings and detailed description of the invention.

BRIEF DESCRIPTION OF THE DRAWINGS

For a fuller understanding of the nature and object of the present invention, reference is made to the accompanying drawings, wherein.

DETAILED DESCRIPTION

Figure 1:
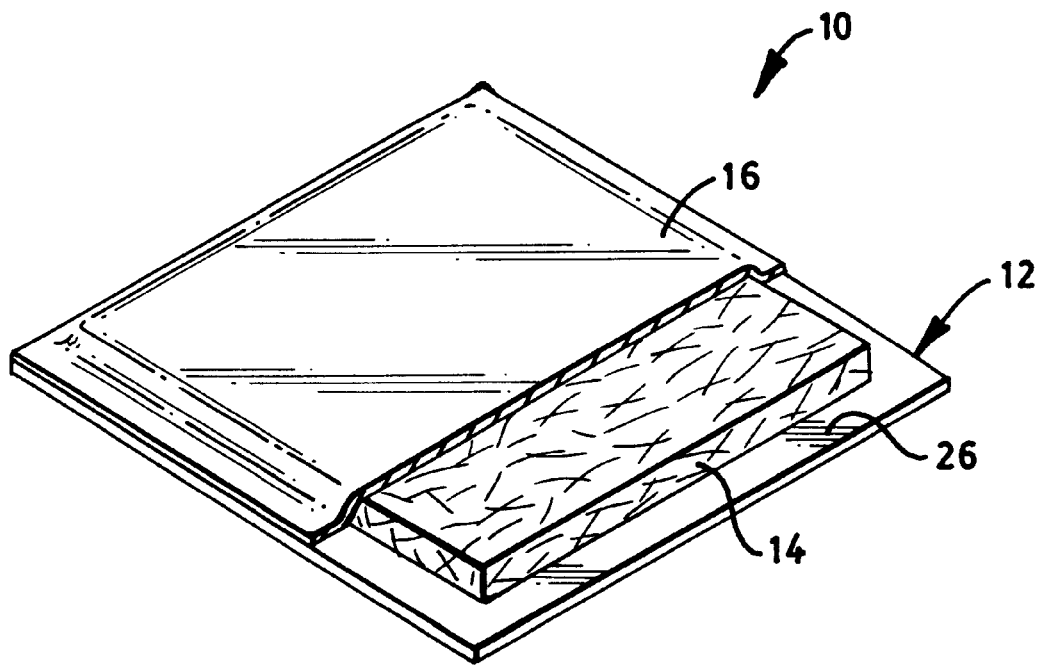
FIG. 1 is a perspective cut-away view of the wipe of the present invention.
Figure 2:
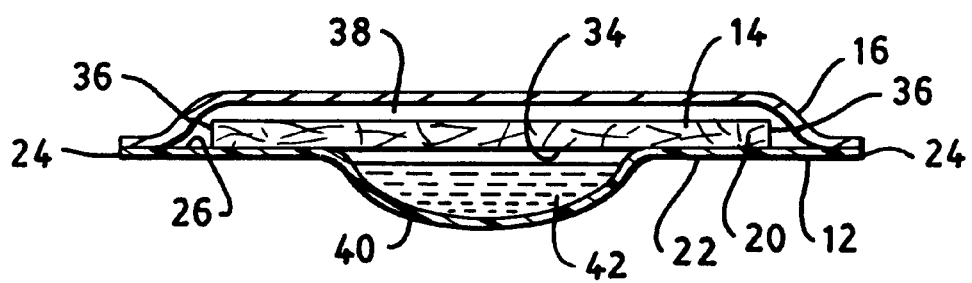
FIG. 2 is a cross-sectional view of the wipe of FIG. 1.

The wetted, disposable wipe 10 of the present invention is constructed by bonding a layer 14 of absorbent material to one side of an impermeable barrier 12, filling a reservoir 40 with a desired dermatological fluid, and sealing the absorbent layer 14 so that the fluid does not evaporate and the absorbent layer 14 maintains its sterility.

The barrier 12 is a sheet that has an absorbent layer surface 20, a handle surface 22, a fluid reservoir 40, and four peripheral edges 24. The barrier 12 is composed of materials that are pliant and which conform to external stresses. The barrier 12 is impervious and impermeable to infectious agents, and is not wettable by water and is insoluble in water, body fluids, and solutions of common dermatological fluids, such isopropyl alcohol.

Typical flexible, impermeable sheets are synthetic resin films. These resin films include polyolefins and polyvinyl copolymers, such as polyethylene, polypropylene, polybutylene, polyvinyl acetate, polyvinyl chloride, polyvinylchloride-vinylidene chloride and the like. The chlorinated polyvinyl copolymers are highly resistant to degradation caused by exposure to either water- or alcohol-based fluids. A barrier 12 made from these materials is flexible, has strength characteristics sufficient to resist tearing and piercing under normal manufacturing and handling stresses, is nonwettable by water, and can be sterilized and colored. The preferred thickness of the barrier 12 is from about 0.5 mils to about 15 mils, and the most preferred thickness is from about 3 mils to about 8 mils.

Figure 3:
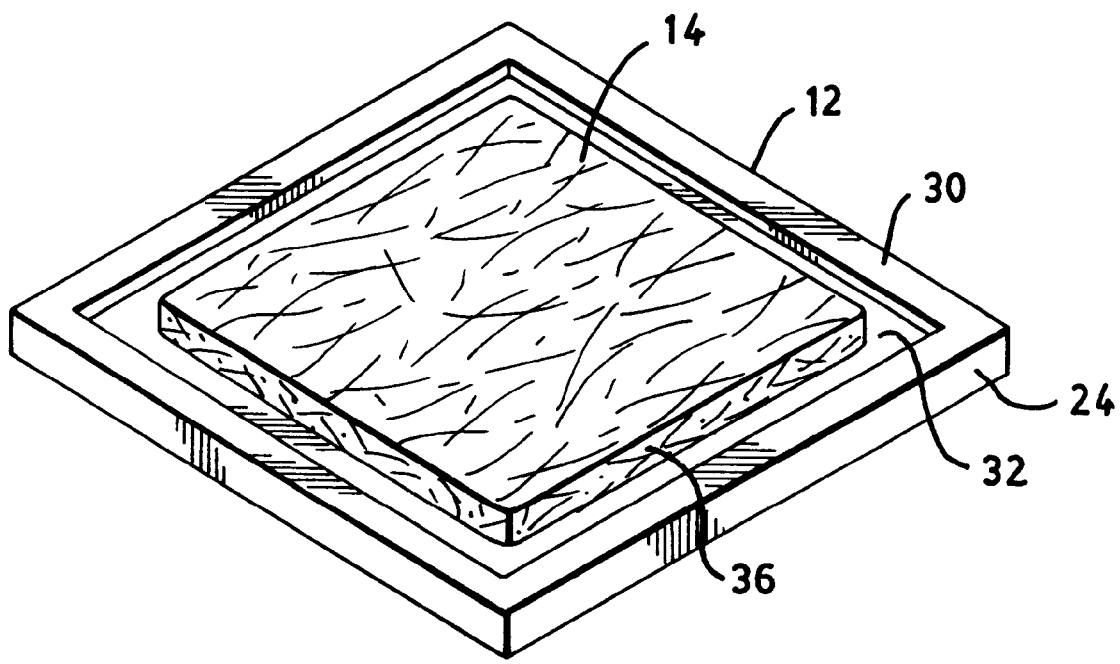
FIG. 3 is a perspective view of the ridge embodiment of the barrier with the absorbent layer.

Merely securing an impermeable barrier 12 to an absorbent layer 14 will not necessarily prevent body fluids from migrating from one side of the wipe to the other at the peripheral edges 24. Migration can occur in both directions, from the absorbent layer 14 to the handle surface 22 of the wipe, or from the person holding the wipe 10 to the absorbent layer 14. The reason is that when the peripheral edges 24 of the barrier 12 are contiguous with the peripheral edges 36 of the absorbent layer 14, body fluids can and will seep or wick around the peripheral edges of the barrier and reach the opposite surface of the wipe 10. To prevent this migration, the present invention uses an absorbent layer 14 with an area that is smaller than that of the barrier 12. The peripheral edges 36 of the absorbent layer 14 are spaced inwardly from the peripheral edges 24 of the barrier 12. This arrangement provides a surrounding zone 26 of the impermeable barrier alone, preventing the migration of body fluids around the peripheral edges 24 of the barrier 12. Hence, any viruses or infectious agents that might be present in the body fluids will be confined to only one side of the wipe 10. Consequently, the bare or glove-covered skin of a health-care worker will not contact any infectious agents that might be present in the body fluids of a patient. Similarly, any infectious agents from the skin of a health-care worker will not be able to contaminate the skin of the patient. optionally, the barrier 12 is reinforced on its periphery with a peripheral ridge 30 around the edges 24 on one or both surfaces of the barrier 12, as in FIG. 3. Adding a peripheral ridge 30 to the absorbent layer surface 20 of the barrier 12 creates a surrounding moat 32 between the peripheral ridge 30 and the entire peripheral edge 36 of the absorbent layer 14. This moat 32 provides an additional trap so that body fluids on one side of the wipe 10 will not migrate around edges of the barrier 12. The peripheral ridge 30 also helps to prevent the collapse of the nonwettable periphery of the barrier 12. The thickness and width of the ridge 30, however, must not be of such magnitude that the ridge 30 substantially impairs the flexibility of the whole wipe 10. Preferably, the ridge 30 is also made out of a polymeric material that is nonwettable by water, impermeable to infectious agents, and insoluble in body fluids and solutions of common dermatological fluids.

The peripheral ridge 30 is integrally formed with the underlying barrier 12 in one of two ways. The ridge 30 can be created by folding up the edges of the barrier sheet or it can be formed by molding the barrier sheet with a thicker edge. Alternatively, the ridge 30 is formed independently from the underlying barrier 12 and is later bonded to the barrier sheet. The independent ridge can be made of the same material as the underlying barrier 12 or of a different polymeric material. Preferably, the peripheral ridge 30, also of chlorinated polyvinyl copolymers, is secured along the peripheral edges 24 of the barrier by thermal, friction, or ultrasonic means well known in the art.

Typically, a wipe 10 has overall dimensions of approximately 2 inches by 2 inches, that is, the barrier 12 has dimensions of approximately 2 inches by 2 inches. This is a convenient size for applying pressure or in wiping body fluids from the skin puncture or needlestick sites of a patient after the administration of an injection or a venipuncture procedure. The absorbent layer 14 typically has overall dimensions of about 1½ inches by 1½ inches. When this size absorbent layer 14 is centrally positioned on the barrier 12, the wipe has a surrounding zone 26, consisting of the barrier alone, of about ¼ inch. Of course, it is possible to adopt various other sizes and shapes for the wipes, such as rectangular, circular, oval, or a combination of such shapes. Similarly, sizes and shapes of the absorbent layer 14 and its position on the barrier 12 can vary according to use and accepted practice in the medical and hygiene arts, as long as there is a zone 26 of the barrier alone that completely surrounds the peripheral edges 36 of the absorbent layer 14.

The absorbent layer 14 is composed of a porous material, such as gauze cotton, prepared cotton, other organic fibers such as wood fibers, rayon, open-meshed cloth of varying degrees of fineness, woven and non-woven synthetic fibers, and foamed polymers such as polyurethane. These materials maintain their integrity when moistened. Typically, the thickness of the absorbent layer 14 ranges from about ¹⁄₆₄ inch to ⅝ inch, depending upon the material and area of the wipe. Generally, the smaller the area of the wipe 10, the thinner the absorbent layer 14.

The method for bonding the absorbent layer 14 to the barrier depends upon the materials of which the barrier 12 and absorbent layer 14 are made, and is accomplished by standard techniques well known in the art of adhesives. The bond is resistant to degradation caused by exposure to the absorbent layer dermatological fluid. To achieve a good bond, it is a common practice to first degrease or rinse the absorbent layer surface 20 of the barrier 12 by an organic solvent such as acetone or methyl ethyl acetone. Degreasing prepares the surface 20 for bonding.

Because the preferred absorbent materials are porous, capable of absorbing liquefied polymer, and allow the evaporation of vapor, most of the standard joining methods using adhesives with or without solvents can be used. A preferred method for joining the barrier 12 to the absorbent layer 14 is to apply a thin coat of a molten polyolefin, such as polyethylene, polypropylene, or polybutylene, onto the absorbent layer surface 20 by extrusion, apply the absorbent layer 14 contiguously to the absorbent layer surface 20, and press them together before the coat solidifies. Alternatively, instead of applying a thin coat of polyolefin by extrusion, the standard rolling technique of direct gravure can be used to print the thin coat to selected areas of the absorbent layer surface 20. Optionally, the barrier surface 34 of the absorbent layer 14 is precoated with a polymer. The molten polyolefin absorbed into the absorbent layer 14 will anchor to the barrier 12 and, when cooled, will bind the absorbent layer 14 and the barrier 12 together.

Alternatively, the absorbent layer 14 is joined to the barrier 12 by applying a solid powder polyolefin to the absorbent layer surface 20 of the barrier 12, placing the absorbent layer 14 on top of the powder, and subjecting the two to a high-pressure heat seal.

The wetted absorbent layer 14 is sealed into an enclosed space 38 between the barrier 12 and a removable cover 16. The space 38 is hermetic so that the absorbent layer 14 remains wetted and uncontaminated by external agents. The space 38 remains hermetic for an extended period of time, for example, one year. This period of time represents the shelf life of the wipe, which includes the period of time from the installation of the cover 16, through transportation and storage, to use, when the cover 16 is removed.

The cover 16 is a planar sheet that is preferably composed of a foil of metal such as an aluminum alloy, a plastic, or a laminate of metal and plastic. The cover 16 is robust enough to maintain integrity while being subjected to normal stresses throughout transportation, storage, and handling. The cover 16 is unaffected by water and the wetting dermatological fluid during the shelf life of the wipe 10.

The adhesive used to adhere the cover 16 to the barrier 12 is strong enough to maintain the hermetic seal, but weak enough so that a small amount of tensional stress, such as that caused by manually peeling the cover 16 from the barrier 12, will cause the adhesive to fracture, allowing the cover 16 to be separated from the barrier 12. The adhesive is unaffected by water and the wetting dermatological fluid during the shelf life of the wipe 10. Since there are currently no satisfactory cold sealing methods that are resistant to alcohol, a typical dermatological fluid, the preferred adhesives include a low-melting-point, toluene-treated polyolefin. For a polyolefin, a low melting point is in the range of from approximately 220°–260° F. Consequently, heat must be applied to the adhesive so that the adhesive can be applied to the barrier and/or cover when installing the cover.

Optionally, there is a tab extending from one edge of the cover 16 that can be grasped between a thumb and finger for ease and convenience in removing the cover 16 from the barrier 12.

One aspect of the wipe 10 of the present invention is that the absorbent layer 14 is prewetted, that is, it is already wetted when opened by the person using the wipe 10. As discussed above, temperatures in the range of 220°–260° F. are needed to seal the cover 16 to the barrier 12. Alcohol, a common dermatological fluid used to wet the absorbent layer, has a very low flash point, the temperature at which the fluid gives off enough vapor to become ignitable. The flash point of isopropyl alcohol is 53° F. and that of ethyl alcohol is 55° F., classifying the fluids as flammable and requiring precautions. Consequently, without precautions, the act of sealing the cover to the barrier has the potential to cause the alcohol vapor to ignite.

The present invention greatly reduces the ignition problem by temporarily storing the wetting fluid 42 in a reservoir 40 while the barrier 12 and cover 16 are being sealed together. The reservoir 40 is a pouch formed in the barrier sheet 12 and centered approximately in the center of the absorbent layer 14. The reservoir 40 is filled with the dermatological fluid 42 either prior to or after the absorbent layer 14 is bonded to the barrier 12. If filled after, the dermatological fluid 42 is injected into the reservoir 40 through the absorbent layer 14 using, for example, a syringe or similar device. The barrier 12 and cover 16 should be sealed together relatively quickly after the reservoir 40 is filled. With contact between the dermatological fluid 42 and the absorbent layer 14 occurring as the wipe 10 is moved, the dermatological fluid 42 will definitely be absorbed into the absorbent layer 14 before the wipe 10 is needed for use.

The wipe 10 is held by a person on the handle surface 22 of the barrier 12. There are several contemplated alternatives in which a handle is provided. In the first, the flexibility of the wipe 10 allows a person to merely grasp the barrier, causing the wipe 10 to crumple between the fingers and providing a handle. In the second alternative, a flap extending from the barrier handle surface 22 provides a handle. In the third alternative, another layer of absorbent material is bonded to the barrier handle surface 22. This "grasping layer" is not prewetted and provides a nonslip surface for grasping. In the fourth alternative, the reservoir pouch extending away from the handle surface 22 is used as a handle. If the pouch is flexible, the material of the empty pouch is bunched together in the center of the barrier to form a handle. If the pouch is somewhat rigid, the outer surface of the pouch may textured to provide a non-slip surface.

Thus it has been shown and described a prewetted, disposable wipe which satisfies the objects set forth above.

Since certain changes may be made in the present disclosure without departing from the scope of the present invention, it is intended that all matter described in the foregoing specification and shown in the accompanying drawings be interpreted as illustrative and not in a limiting sense.

What is claimed is:

1. A wipe comprising:
   a. a barrier composed of a sheet that is impermeable to infectious agents and having a surrounding peripheral edge;
   b. an absorbent layer secured to said barrier and having a surrounding peripheral edge and a prewetted area smaller than said barrier;
   c. a reservoir in said barrier adjacent to said absorbent layer, said reservoir being filled with a dermatological fluid that is subsequently absorbed by said absorbent layer prior to use;
   d. absorbent layer securing means for securing said absorbent layer to said barrier, said absorbent layer being located on said barrier such that said absorbent layer peripheral edge is spaced inwardly from said barrier peripheral edge, providing a zone of said barrier surrounding said absorbent layer;
   e. a cover composed of a thin, flexible sheet having approximately the same shape and area as said barrier; and
   f. cover securing means for securing said cover to said barrier zone such that said absorbent layer is contained within a hermetically closed space between said barrier and said cover, said cover securing means including the use of heat that has a temperature higher than the flash point of said dermatological fluid, said cover securing means having a tensional stress resistance that permits manual removable of said cover from said barrier.

2. The wipe of claim 1 wherein said absorbent layer securing means is resistant to degradation by said dermatological fluid for at least a predetermined period of time.

3. The wipe of claim 1 wherein said absorbent layer securing means is a polyolefin adhesive.

4. The wipe of claim 1 wherein said cover securing means is resistant to degradation by said dermatological fluid for at least a predetermined period of time.

5. The wipe of claim 1 wherein said cover securing means is an adhesive composed substantially of a low-melting-point, toluene-treated polyolefin.

6. The wipe of claim 1 wherein said barrier zone includes a peripheral ridge rising from said barrier zone surface.

7. A wipe comprising:
   a. a barrier composed of a sheet that is impermeable to infectious agents and having a surrounding peripheral edge;
   b. an absorbent layer secured to said barrier and having a surrounding peripheral edge and a prewetted area smaller than said barrier;
   c. a reservoir in said barrier adjacent to said absorbent layer, said reservoir being filled with a dermatological fluid that is subsequently absorbed by said absorbent layer prior to use;
   d. absorbent layer securing means for securing said absorbent layer to said barrier, said absorbent layer being located on said barrier such that said absorbent layer peripheral edge is spaced inwardly from said barrier peripheral edge, providing a zone of said barrier surrounding said absorbent layer, said absorbent layer securing means being resistant to degradation by said dermatological fluid for at least a predetermined period of time;
   e. a cover composed of a thin, flexible sheet having approximately the same shape and area as said barrier; and
   f. cover securing means for securing said cover to said barrier zone such that said absorbent layer is contained within a hermetically closed space between said barrier and said cover, said cover securing means including the use of heat having a temperature higher than the flash point of said dermatological fluid, said cover securing means having a tensional stress resistance that permits manual removable of said cover from said barrier, said cover securing means being resistant to degradation by said dermatological fluid for at least a predetermined period of time.

8. The wipe of claim 7 wherein said absorbent layer securing means is a polyolefin adhesive.

9. The wipe of claim 7 wherein said cover securing means is an adhesive composed substantially of a low-melting-point, toluene-treated polyolefin.

10. The wipe of claim 7 wherein said barrier zone includes a peripheral ridge rising from said barrier zone surface.

11. A wipe comprising:
   a. a barrier composed of a sheet that is impermeable to infectious agents and having a surrounding peripheral edge;
   b. an absorbent layer secured to said barrier and having a surrounding peripheral edge and a prewetted area smaller than said barrier;
   c. a reservoir in said barrier adjacent to said absorbent layer, said reservoir being filled with a dermatological fluid that is subsequently absorbed by said absorbent layer prior to use;
   d. a polyolefin absorbent layer adhesive for securing said absorbent layer to said barrier, said absorbent layer being located on said barrier such that said absorbent layer peripheral edge is spaced inwardly from said barrier peripheral edge, providing a zone of said barrier surrounding said absorbent layer, said absorbent layer adhesive being resistant to degradation by said dermatological fluid for at least a predetermined period of time;
   e. a cover composed of a thin, flexible sheet having approximately the same shape and area as said barrier; and
   f. a low-melting-point, toluene-treated polyolefin cover adhesive for securing said cover to said barrier zone such that said absorbent layer is contained within a hermetically closed space between said barrier and said cover, said cover adhesive needing heat in order to apply said cover adhesive to secure said cover to said barrier zone, said heat having a temperature higher than the flash point of said dermatological fluid said cover adhesive having a tensional stress resistance that permits manual removable of said cover from said barrier, said cover adhesive being resistant to degradation by said dermatological fluid for at least a predetermined period of time.

12. The wipe of claim 11 wherein said barrier zone includes a peripheral ridge rising from said barrier zone surface.

* * * * *